United States Patent
Andersson

(10) Patent No.: US 8,787,607 B2
(45) Date of Patent: Jul. 22, 2014

(54) PERCUTANEOUS BONE CONDUCTION IMPLANT

(75) Inventor: Marcus Andersson, Göteborg (SE)

(73) Assignee: Cochlear Limited, Macquarie University, NSW (AU)

(*) Notice: Subject to any disclaimer, the term of this patent is extended or adjusted under 35 U.S.C. 154(b) by 512 days.

(21) Appl. No.: 12/732,155

(22) Filed: Mar. 25, 2010

(65) Prior Publication Data

US 2010/0286776 A1 Nov. 11, 2010

(30) Foreign Application Priority Data

Mar. 25, 2009 (DE) .................. 10 2009 014 771

(51) Int. Cl.
*H04R 25/00* (2006.01)
(52) U.S. Cl.
USPC .......................... 381/326; 606/308
(58) Field of Classification Search
USPC .......................... 381/326; 606/308
See application file for complete search history.

(56) References Cited

U.S. PATENT DOCUMENTS

| | | | |
|---|---|---|---|
| 4,498,461 A * | 2/1985 | Hakansson | 600/25 |
| 4,776,322 A * | 10/1988 | Hough et al. | 381/326 |
| 5,263,930 A * | 11/1993 | Ensminger | 604/288.03 |
| 5,338,287 A * | 8/1994 | Miller et al. | 600/25 |
| 5,456,654 A * | 10/1995 | Ball | 600/25 |
| 5,951,601 A * | 9/1999 | Lesinski et al. | 623/10 |
| 6,436,084 B1 * | 8/2002 | Finch et al. | 604/506 |
| 6,940,989 B1 * | 9/2005 | Shennib et al. | 381/326 |
| 7,409,070 B2 * | 8/2008 | Pitulia | 381/326 |
| 2006/0126874 A1 * | 6/2006 | Westerkull | 381/326 |
| 2009/0082817 A1 * | 3/2009 | Jinton et al. | 606/301 |

FOREIGN PATENT DOCUMENTS

| | | |
|---|---|---|
| SE | 531177 C2 | 1/2009 |
| WO | 0209622 A1 | 2/2002 |
| WO | 2004105650 A1 | 12/2004 |
| WO | 2008/143574 A1 | 11/2008 |

* cited by examiner

*Primary Examiner* — Forrest M Phillips
(74) *Attorney, Agent, or Firm* — K&L Gates, LLP

(57) ABSTRACT

One embodiment relates to a percutaneous bone conduction implant. The implant includes a fixture configured to be anchored in the recipient's skull, and a skin-penetrating abutment configured to interface with the fixture and to permit the abutment to be removably attached to the fixture to form a fixture-abutment assembly. In an embodiment, at least one anti-microbial surface forms one or more surfaces of the formed fixture-abutment assembly located in an interior of the formed fixture-abutment assembly when the fixture is removably attached to the abutment with an abutment screw. The interior is substantially isolated from a surrounding environment of the fixture-abutment assembly.

33 Claims, 2 Drawing Sheets

PERCUTANEOUS BONE CONDUCTION IMPLANT

CROSS-REFERENCE TO RELATED APPLICATIONS

This Patent Application claims foreign priority to German Patent Application No. 102009014771.3, entitled "Hearing Aid Implant," filed on 25 Mar. 2009, which is hereby incorporated herein by reference herein.

BACKGROUND

1. Field of the Invention

The present invention relates generally to hearing prosthesis and, more particularly, to a percutaneous bone conduction implant.

2. Related Art

For persons who cannot benefit from traditional acoustic hearing aids, there are other types of commercially available hearing prostheses such as, for example, bone conduction hearing prostheses (also referred to as "bone conduction hearing aids," and "bone conduction devices;" "bone conduction devices" herein). Bone conduction devices mechanically transmit sound information to a person's inner ear by transferring vibrations to person's skull. This enables the hearing prosthesis to be effective regardless of whether there is disease or damage in the middle ear.

Traditionally, bone conduction devices transfer vibrations from an external vibrator to the skull through a bone fixture that penetrates the skin and is physically attached to both the vibrator and the skull. Typically, the external vibrator is connected to the percutaneous bone conduction implant located behind the external ear so that sound is transmitted via the skull to the cochlea. Generally, the percutaneous bone conduction implant connecting the bone conduction device (the portion containing the vibrator) to the skull generally comprises two components: a bone attachment piece (e.g., bone fixture/fixture) that is attached or implanted directly into the skull, and a skin penetrating piece attached to the bone attachment piece (often referred to as an abutment).

SUMMARY

According to one embodiment of the present invention, there is a percutaneous bone conduction implant that includes a fixture configured to be anchored in the recipient's skull. The percutaneous bone conduction implant further includes a skin-penetrating abutment configured to interface with the fixture and to permit the abutment to be removably attached to the fixture to form a fixture-abutment assembly. In an embodiment, at least one anti-microbial surface forms one or more surfaces of the formed fixture-abutment assembly located in an interior of the formed fixture-abutment assembly when the fixture is removably attached to the abutment with an abutment screw. In this embodiment, the interior is substantially isolated from a surrounding environment of the fixture-abutment assembly.

According to another embodiment of the present invention, there is a percutaneous bone conduction implant, comprising a fixture configured to be anchored in the recipient's skull. The implant further comprises a skin-penetrating abutment configured to interface with the fixture and to permit the abutment to be removably attached to the fixture to form a fixture-abutment assembly. In an embodiment, the abutment includes a first coupling portion adapted to receive a second coupling portion of a bone conduction device and to establish a mechanical connection with the bone conduction device. Further, at least one anti-microbial surface is present in the formed fixture-abutment assembly and located in an interior of the formed fixture-abutment assembly when the fixture is removably attached to the abutment with an abutment screw, the interior being substantially isolated from a surrounding environment of the fixture-abutment assembly.

BRIEF DESCRIPTION OF THE DRAWINGS

Embodiments of the present invention are described herein with reference to the attached drawing sheets in which.

DETAILED DESCRIPTION

Figure 1:
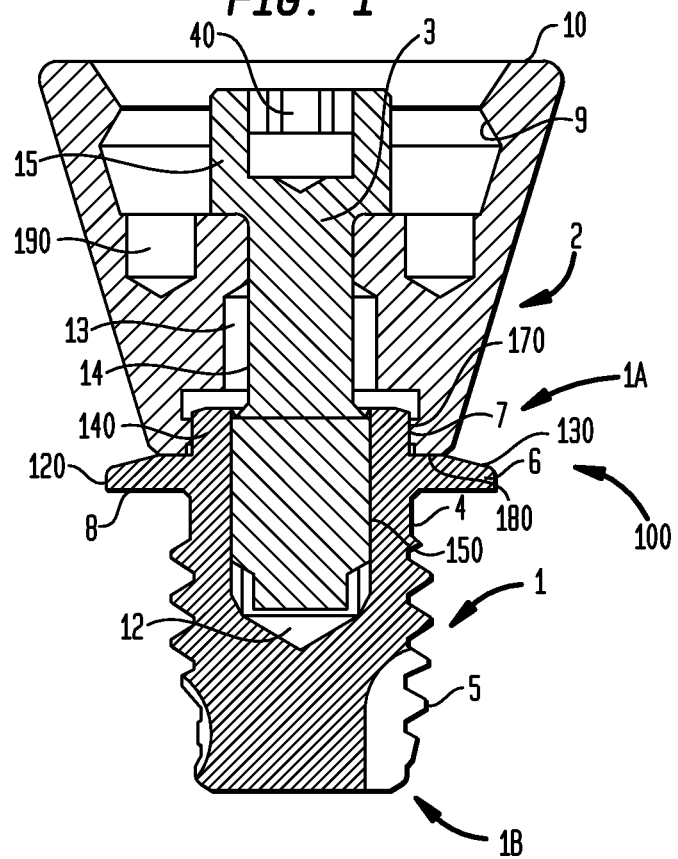
FIG. 1 is a cross-sectional view of a percutaneous bone conduction implant provided with an anti-microbial coating, in accordance with embodiments of the present invention.

In an embodiment, there is a percutaneous bone conduction implant for anchorage of a bone conduction device to a recipient's skull. The percutaneous bone conduction implant includes a fixture configured to be implanted in the recipient's skull, and a skin-penetrating abutment configured to detachably interface with the fixture to form a fixture-abutment assembly. Controlled vibrations generated by the bone conduction device may be transmitted from outside the recipient's body directly into the fixture-abutment assembly, and into a recipient's skull. In an embodiment, at least one anti-microbial surface forms one or more surfaces of the formed fixture-abutment assembly. The anti-microbial surface may be located in an interior of the formed fixture-abutment assembly when the fixture is removably attached to the abutment, the interior being substantially isolated from a surrounding environment of the percutaneous bone conduction implant.

More particularly, aspects and exemplary embodiments disclosed herein are generally directed to a percutaneous bone conduction implant in which the surfaces of a fixture (corresponding to a bone attachment piece) and an associated abutment (corresponding to a skin penetrating piece) are provided with an anti-microbial coating configured to reduce and/or eliminate undesirable micro-leakage of bacteria (hereinafter "micro-leakage) which may be caused, by way of example only and not by way of limitation, by gaps between mating surfaces of the fixture, the abutment, and/or the abutment screw. These gaps may be present due to imperfections in the mating surfaces, deficiencies in the tightening torques provided to the abutment screw (e.g. failure to properly initially implant the percutaneous bone conduction implant), misalignment of the abutment with the fixture component, etc. (e.g. where a gap was present beginning at implantation of the implant), These gaps may also be present as an intractable feature resulting from use and/or age of a percutaneous bone conduction implant (e.g. the gap may initially not be present in the percutaneous bone conduction implant, but, after a number of years of use, a gap is opened creating a micro-leakage path).

In certain embodiments, the percutaneous bone conduction implant has a smooth outer contour facing the surrounding soft tissue of the skin to minimize unwanted pockets or gaps in the tissue-device interface. In some embodiments, the regions of the fixture and the abutment which mate with each other have inverse conically-shaped regions such that, when mated, the fixture forms the bottom of an hourglass shape while the abutment forms the top of the hourglass shape. In other embodiments, the regions of the fixture and the abutment which mate with each other have respective mating surfaces that extend at right-angles to each other. In some embodiments, the fixture forms the bottom leg of a "Y" shape and the abutment forms the top legs of the "Y" shape. In an embodiment, dimensions of the hourglass shape configuration and the "Y" shaped configuration are such that the recipient's skin abuts the narrow region of the hourglass configuration and the intersection of the legs of the "Y" shape configuration, respectively.

In certain embodiments, the upper end face of the fixture has an open cavity with a tapered interior surface forming a seat for the tapered exterior side wall of the abutment. In other embodiments, the bottom end face of the abutment has an open cavity with a cylindrical interior surface forming a female seat for a cylindrical exterior male portion of the fixture. These configurations may create a good connecting fit between the fixture and abutment so as to reduce the risk of micro-leakage.

Percutaneous bone conduction implants suffer from risks of infection and inflammation at the skin-implant interface resulting from bacterial colonization in the area around the interface. An embodiment of the percutaneous bone conduction implant disclosed herein increases the integration of the skin to the percutaneous bone conduction implant thereby decreasing the likelihood that a gap will form between the two. Such gaps are, unfortunately, an ideal environment for the bacteria. By creating an integration of the skin to the percutaneous bone conduction implant the adverse skin reactions associated with bone anchored percutaneous bone conduction implants may be reduced.

Integration between the skin and the implant occurs when the soft tissue encapsulates the implant in fibrous tissue and does not readily dissociate itself from the implant. U.S. Provisional Patent Application No. 60/951,163, entitled "Bone Anchor Fixture for a Medical Prosthesis," filed Jul. 20, 2007, discloses a surface modification which reduces certain adverse skin reactions, and which may be implemented in embodiments of the present invention. The contents of U.S. Provisional Patent Application No. 60/951,163 in general, and the surface modification disclosed therein in particular, is hereby incorporated by reference for application to some embodiments disclosed herein, conceptually and/or exactly, to reduce and/or eliminate adverse skin reactions associated with bone anchored percutaneous bone conduction implants. In other embodiments the abutment is coated to reduce the shear modulus, as described in greater detail below.

Embodiments of the percutaneous bone conduction implant may be used in connection with systems where sound is transmitted via the skull directly to the inner ear of a person with impaired hearing. However, embodiments of the percutaneous bone conduction implant may also be configured for use in connection with other types of systems with components anchored in the skull and for ear or orbital prostheses which are also anchored in the skull. Other applications of the percutaneous bone conduction implant are also contemplated.

Figure 2:
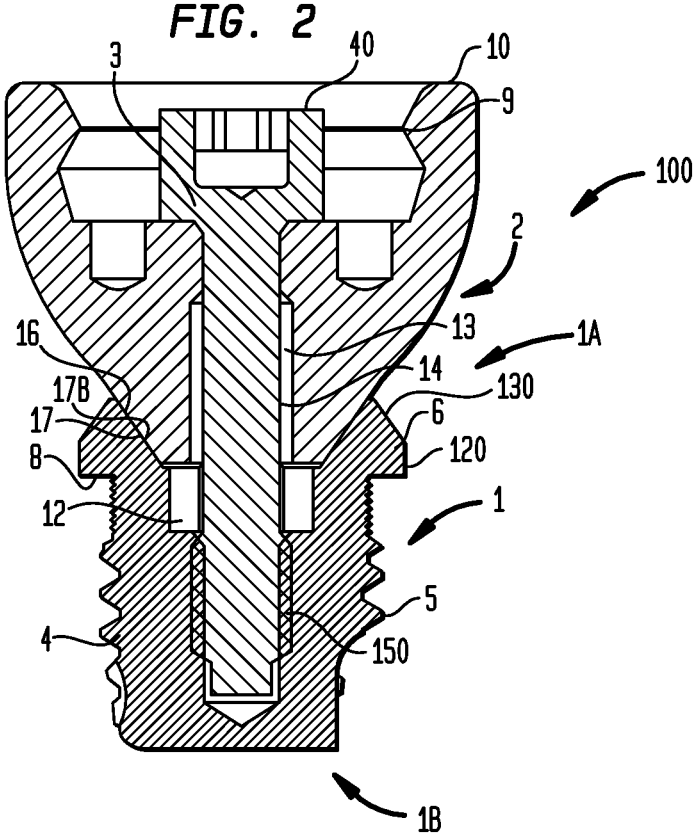
FIG. 2 is a cross-sectional view of another percutaneous bone conduction implant provided with an anti-microbial coating, in accordance with embodiments of the present invention.
Figure 3:
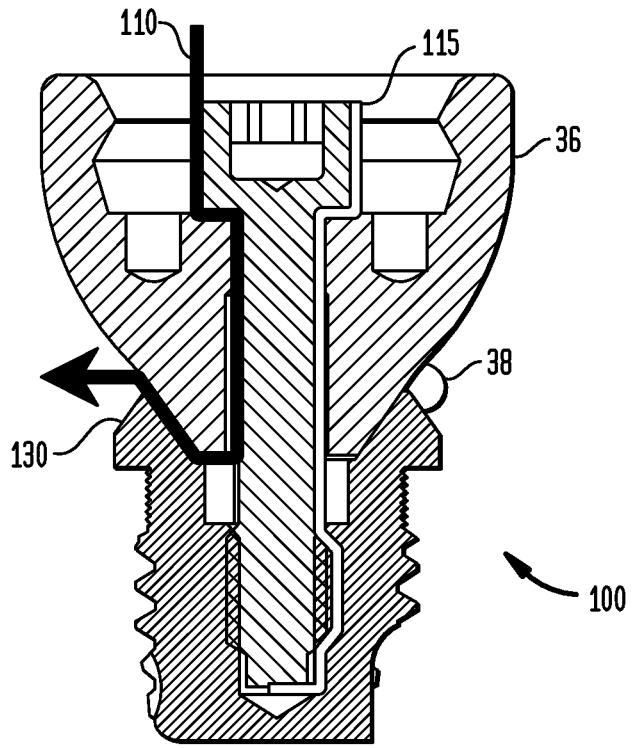
FIG. 3 is cross-sectional side view of the percutaneous bone conduction implant of FIG. 2 illustrating an exaggerated possible micro-leakage path and an exaggerated anti-microbial coating.

FIGS. 1-3 depict a cross-sectional view of a bone anchored percutaneous bone conduction implant 100 according to exemplary embodiments of the present invention. Percutaneous bone conduction implant 100 is illustrated in FIGS. 1-3 with a screw-shaped fixture 1 and a skin-penetrating abutment 2. These two components are connected by an elongate coupling shaft or an abutment screw 3 having, in one embodiment, a cylindrical screw head 40. Screw head 40 has an internal hex or multi-lobular configuration for a cooperating insertion tool (not illustrated here). In an alternate embodiment, screw head 40 may instead or in addition to the internal hex head utilize an external hex geometry.

Fixture 1 may be made of any material that has a known ability to integrate into surrounding bone tissue (i.e., it is made of a material that exhibits acceptable osseointegration characteristics). (This may also be the case with respect to the abutment 2, in some embodiments.) In one embodiment, fixture 1 includes a main body 4. In an embodiment, the fixture 1 is made of titanium. Fixture 1 has a main body 4 with an outer screw thread 5 which is configured to be installed into the skull. Fixture 1 also comprises a flange 6 configured to function as a stop when fixture 1 is installed into the skull. Flange 6 prevents the screw thread 5 from completely penetrating through the skull. Fixture 1 may further comprise a tool-engaging socket having an internal grip section for easy lifting and handling of fixture 1. Tool-engaging socket and the internal grip section are described and illustrated in U.S. Provisional Application No. 60/951,163, entitled "Bone Anchor Fixture for a Medical Prosthesis," filed Jul. 20, 2007, the contents of which is hereby incorporated by reference herein for application, exactly and/or conceptually, to installing and manipulating the fixture 1.

The main body 4 of fixture 1 may have length sufficient to securely anchor the fixture 1 into the skull without penetrating entirely through the skull. The length of the main body 4 may therefore depend on the thickness of the skull at the implantation site. In one embodiment, the main body of the fixture 1 has a length that is no greater than 5 mm, measured from the planar bottom surface 8 of the flange 6 to the end of the distal region 1B (this limits and/or prevents the possibility that the main body 4 might go completely through the skull). In another embodiment, the length of the main body is from about 3.0 mm to about 5.0 mm.

In the embodiment depicted in FIG. 1, the main body of fixture 1 has cylindrical proximate end 1A, a straight, generally cylindrical body, and a screw thread 5. The distal region 1B of fixture 1 may be fitted with self-tapping cutting edges formed into the exterior surface of the fixture. Further details of the self-tapping features are described in International Patent Application WO 02/09622, the contents of which is hereby incorporated by reference herein for application, exactly and/or conceptually, to configuring fixture 1 to be installed into a skull.

In the embodiment depicted in FIGS. 2-3, the main body of the fixture 1 has a tapered apical proximate end 1A, a straight, generally cylindrical body, and a screw thread 5. The distal region 1B of fixture 1 may also be fitted with self-tapping cutting edges (e.g., three edges) formed into the exterior surface of the fixture.

A clearance or relief surface may be provided adjacent to the self-tapping cutting edges in accordance with the teachings of U.S. Patent Application Publication No. 2009/0082817, the contents of which is hereby incorporated by reference herein for application to configuring fixture 1 to be installed into a skull. Such a design may reduce the squeezing effect between the fixture 1 and the bone during installation of the screw by creating more volume for the cut-off bone chips.

As illustrated in FIGS. 1-3, flange 6 has a planar bottom surface for resting against the outer bone surface, when anchoring fixture 1 has been screwed down into the skull. Again, flange 6 prevents the fixture 1 from completely penetrating through the skull. Preferably, flange 6 has a diameter which exceeds the peak diameter of the screw threads 5 (the screw threads 5 of the fixture 1 may have an outer diameter of about 3.5-5.0 mm). In one embodiment, the diameter of the flange 6 exceeds the peak diameter of the screw threads 5 by approximately 10-20%. Although flange 6 is illustrated in FIGS. 1-3 as being circumferential, flange 6 may be configured in a variety of shapes so long as flange 6 has a diameter or width that is greater than the peak diameter of the screw threads 6. Also, the size of flange 6 may vary depending on the particular application for which the percutaneous bone conduction implant 100 is intended.

In FIGS. 2-3, the outer peripheral surface of flange 6 has a cylindrical part 120 and a flared top portion 130. The upper end of flange 6 is designed with an open cavity having a tapered inner side wall 17. The tapered inner side wall 17 is adjacent to the grip section (not shown). The interior of the flange 6 further includes an inner bottom bore 150 having internal screw threads for securing a coupling shaft of abutment screw 3.

In FIG. 1, the upper end 1A of fixture 6 is designed with a cylindrical boss 140 having a coaxial outer side wall 170 extending at a right angle from a planar surface 180 at the top of flange 6.

In one embodiment, increased stability to the attachment between fixture 1 and abutment 2 is provided as detailed in U.S. Patent Application Publication No. 2009/0082817, the contents of which is hereby incorporated by reference herein for application, conceptually and/or exactly, to providing increased stability to the attachment of the fixture and the abutment implemented in embodiments described herein.

Figure 4:
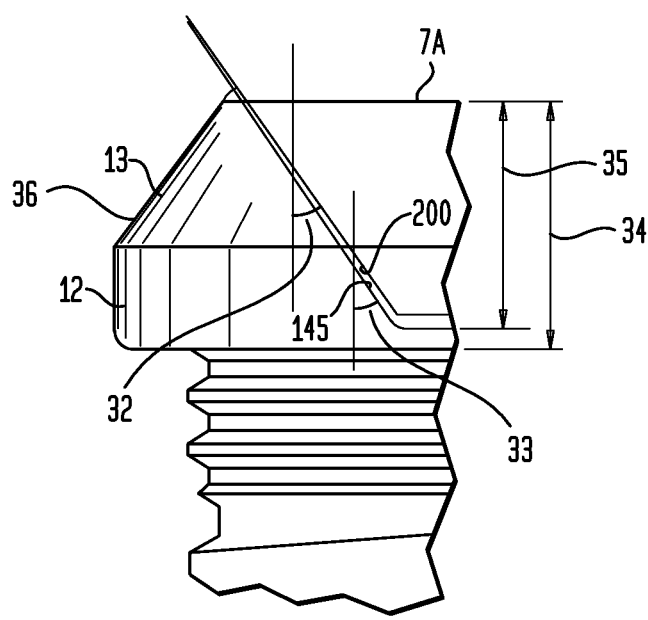
FIG. 4 is a planar partial view of a proximate end of a fixture, illustrating the tapered connection between the fixture and the abutments of the percutaneous bone conduction implant illustrated in FIG. 2.

In the embodiments illustrated in FIGS. 2 and 3, the flange 6 has a smooth, open upper end and does not have a protruding hex. The smooth upper end of the flange 6 and the absence of any sharp corners provides for improved soft tissue adaptation. Flange 6 also comprises a cylindrical part 120 which, together with the flared upper part 130, provides sufficient height in the longitudinal direction for internal connection with the abutment 2. FIG. 4 illustrates the tapered seat 145 seated within the height 34 of flange 6 of the percutaneous bone conduction implant 100 depicted in FIGS. 2 and 3.

It should be appreciated that the fixture 1, abutment 2 and coupling shaft 3, may be delivered separately or they may be delivered in the form of a pre-mounted device as illustrated in WO 2004/105650. In accordance with one embodiment, the percutaneous bone conduction implant 100 is delivered to the surgeon pre-mounted in its package to facilitate installation of the entire device in a single step. Abutment 2 may be pre-mounted to the fixture 1 at the manufacturing site with the correct tightening torque to obviate the need for the surgeon to know the correct tightening torque or to handle the separate pieces of the percutaneous bone conduction implant 100.

In contrast to traditional implants which require an outer fixture hex for tool engagement, the percutaneous bone conduction implant 100 may be installed by using the recesses 190 in the abutment 2. These recesses 190 are located on the upper part of the percutaneous bone conduction implant 100 and are more visible than a traditional outer hex.

According to the embodiment shown in FIGS. 2-3, the abutment 2 has a substantially curved, conical outer surface with an upper edge 10 and a bottom, fixture-connecting part 17B. The upper edge 10 may have a width or diameter that is larger than that of the bottom, fixture connecting part 17B. The bottom part 17B of the outer surface has a contour 16 adapted to be seated with the tapered inner contour 145 of the fixture 1 to create a good connecting fit between the fixture 1 and abutment 2. The two conical shaped surfaces not only provides an axially well-defined fit when assembled together, they also provides for easy disassembly.

In some embodiments, designing the upper part of the fixture 1 and the lower part of the abutment 2 with a conical fit reduces the risk for gaps and unwanted micro-leakage, regardless of any imperfections in the contact surfaces or incorrect tightening torques.

In some embodiments, the abutment 2 is provided with an inner annular flange 9 adjacent upper edge 10 adapted to cooperate with second coupling parts (not shown) of an exterior vibrator (relative to the recipient) through a snap-in action or the like. Attachment of the second coupling parts of the exterior vibrator permits vibration to be directly sent from the vibrator into the percutaneous bone conduction implant/percutaneous bone conduction implant 100.

As shown in FIG. 4, the tapered portion 200 of the abutment 2 is characterized by a cone angle 32. The cone angle 32 is configured so as to securely couple the fixture 1 and the abutment 2 without significant gaps. Preferably, the cone angles 32 and 33 are in the range of about 30° to about 40°, with little or no difference between the cone angles 32 and 33. In one embodiment, the cone angles 32 and 33 are substantially the same. In another embodiment, the difference between the cone angles 32 and 33 is about 1° to about 5°, and more preferably about 1°.

In some embodiments, the reduction of the risk of infections and inflammation that results from bacterial colonization in the unwanted pockets and gaps that are formed between the skin and the implant is addressed. As illustrated in FIG. 3, an hourglass waist angle 38 is generally defined between the exterior peripheral surface 36 of flared portion 13 of flange 6 and the tapered lower portion 16 of abutment 2. The hourglass waist angle 38 provides a smooth outer contour to the facing soft tissue such that unwanted pockets and gaps are not formed between the surrounding tissue and the percutaneous bone conduction implant 30. This smooth contour facilitates integration between the percutaneous bone conduction implant 30 and the surrounding tissue to substantially eliminate gaps and unwanted pockets where bacteria might grow. This is in contrast to many traditional implant devices in which a comparatively sharp interface is formed with the contacting tissue. The embodiment depicted in FIG. 2 show an hourglass waist angle is greater than 90°.

In certain embodiments, the skin-contacting surface of abutment 2 may be modified in such a way that the shear modulus of the skin-contacting part of abutment 2 is reduced to less than 35 GPa. The surface of the skin-contacting part of the percutaneous bone conduction implant abutment 2 may be coated with a biocompatible polymer or a ceramic material. In accordance with one aspect of the embodiments, the coating has a thickness of approximately 0.001-50.0 µm. A surface increasing treatment may be provided resulting in a roughness value $S_a$ of 0.5-10 µm in place of or in addition to the coating. These modifications to the skin-contact surface generally reduce the shear modulus and certain adverse skin reactions. Surface modifications of this type are discussed in more detail in the co-pending patent application incorporated by reference elsewhere herein.

In certain embodiments, the abutment is coated with a material to reduce the shear modulus. Such a material may be, for example, a biocompatible polymer, a ceramic material, and/or a combination thereof. In one specific embodiment, the material has a thickness of about 0.001 μm to about 50.0 μm. In the same or other embodiments, the shear modulus is reduced to less than 35 GPa. In the same or other embodiments, the abutment is coated with a surface increasing material. Such a material may be such that it provides a roughness value of about 0.5 μm to about 10 μm. Further details of the above and other features may be found in Swedish Patent Application No. 0701244-6, which is hereby incorporated by reference herein.

The percutaneous bone conduction implant 100 may also be designed in such a way that it is easy to handle together with instruments and components used for installation and control of the implant device. As noted, surgical techniques normally used for installing the implants have been carried out as a two-step procedure. In the first step the implant is inserted and maintained unloaded during a healing period of about a couple of months. During this healing period it is important to avoid micro-leakage from the percutaneous bone conduction implant and bacteria colonization.

As detailed above, abutment screw 3 is utilized to connect abutment 2 to fixture 1 to form a mechanically tight seal between the abutment 2 and the fixture 1, to limit and/or eliminate micro-leakage in the percutaneous bone conduction implant 100. Unfortunately, sometimes a micro-leakage path is still preset, such as micro-leakage path 110, as exemplary depicted in FIG. 3. In an embodiment, anti-microbial agents are applied to one or more surfaces of the abutment 2, the fixture 1 and/or the abutment screw 3, as will now be described. By applying anti-microbial agents to surfaces located in this path, the micro-leakage path 110 can be blocked vis-à-vis bacteria invading the interior of the percutaneous bone conduction implant 100. This prevents bacteria from forming a bacteria reservoir in the interior of the percutaneous bone conduction implant 100 and/or from reaching the exterior of the percutaneous bone conduction implant 100 through the micro-leakage path 110.

In an embodiment, an anti-microbial coating is applied to the abutment screw 3 in the form of a silver coating in concentrations sufficient to kill more than 95%, and in some embodiments more than 99%, and in some embodiments more than 99.9%, of all bacterial that may come into contact with the treated surface.

Herein, a surface having an anti-microbial coating is an anti-microbial surface. Further, a component made from an anti-microbial material has an anti-microbial surface if the anti-microbial material is present in sufficient quantity to have anti-microbial features.

In an embodiment, the anti-microbial coating effectively stops microbes from multiplying and migrating/advancing through the interior of the percutaneous bone conduction implant 100 to the exterior of the percutaneous bone conduction implant 100 through the micro-leakage path 110, thus reducing the number of skin complications associated with implants having the configuration as described herein. Because bacteria tend to live on the surface of a structure, coating interior surfaces of the percutaneous bone conduction implant 100 is an effective approach to reducing/preventing bacterial advancement through the micro-leakage path 110.

In an embodiment, this provides a failsafe feature in the event that the abutment screw 3 loosens (thus opening a gap through which microbes may advance) during the time that the percutaneous bone conduction implant 100 is implanted in a skull. Such loosening may occur when the surgeon fails to apply sufficient torque to the abutment screw 3.

Referring to FIGS. 1-3, when fixture 1, abutment 2 and abutment screw 3 are properly mounted together, the interior parts 12 and 13 in the fixture 1 and the abutment 2, respectively are closed inside the percutaneous bone conduction implant 100 and do not face/are not exposed to any surrounding tissue or surrounding atmosphere (i.e., the environment surrounding the percutaneous bone conduction implant 100). Also, during normal implantation, the surface 14 of the abutment screw 3 below the screw head 15 is closed within the implant assembly. In some embodiments, the interior parts are initially hermetically sealed from the exterior environment of the implant assembly, at least until a micro-leakage path is opened.

According to an embodiment, in addition to the mechanically tight fit obtained by the interface of the abutment 2 with the fixture 1 when the abutment screw 3 releasably secures the abutment 2 to the fixture 1 to form a fixture-abutment assembly, an anti-microbial coating is present on surfaces of interior part 13 of the abutment 2 and/or on surfaces of interior part 12 of the fixture 1 and/or on surfaces of part 14 of the abutment screw 3. The interior parts 13 and 12 are those parts of the abutment and fixture that do not face/are not exposed to the tissue or surrounding atmosphere when the components of the percutaneous bone conduction implant 100 are properly mounted. When properly mounted, the environment in the interior of the percutaneous bone conduction implant 100 is closed from the outside of the percutaneous bone conduction implant 100 and thus will remain relatively dry, and elution of any substances contained in the interior is therefore limited. In such instances, it is noted that there is no need for an anti-microbial coating applied to the open interior of the percutaneous bone conduction implant 100 such as, for example, the upper edge 10 of the abutment 2.

By limiting the application of the anti-microbial coating to interior surfaces in some embodiments, and thus generally shielding the soft tissue from exposure to the anti-microbial coating at least until necessary, the general risk inherent in using anti-microbial treatments—that the microbes develop a resistance to the treatment—is reduced. Also, silver contact with the bone may have a deleterious effect on the bone. Sliver contact with the bone is reduced by limiting the coating to the interior of the percutaneous bone conduction implant 100. Further, by containing the silver based anti-microbial coating to the interior of the percutaneous bone conduction implant 100, negative effects on the soft tissue may be reduced as well (e.g., silver sometimes discolors skin).

FIG. 3 depicts an exemplary embodiment where an anti-microbial coating 115 is applied to surfaces of the abutment screw 3. (Note that element 115 is only depicted in FIG. 3 as being present on one side of the abutment screw 3, this for convenience of depicting the hypothetical micro-leakage path 110—in practice, the coating 115 could be present all the way around the abutment screw 3, at least in the areas of the screw 3 opposite the abutment 2 (e.g., in the area of interior part 13)).

In one embodiment, the anti-microbial agent used to form the coating is a substance which is tightly bound to the respective surfaces of the percutaneous bone conduction implant 100 and does not leach out to the tissue. In an embodiment, the anti-microbial effect is confined to the respective surface or surface interface and thus need not be a dose dependent drug elution.

In one embodiment, the anti-microbial coating comprises a surface bound silver or silver containing compound. Silver is considered safe and is used in several medical device applications, such as by way of example only and not by way of limitation, wound dressings and catheters. However, there are several other elemental substances that might have a similar effect including iodine, which is a common antiseptic agent. Some embodiments may thus utilize an iodine-based anti-microbial coating.

According to an embodiment, silver is dispersed as small particles to increase the total surface area of the silver compound of the anti-microbial coating. In another embodiment, the silver is dispersed in a carrier (e.g., made of a polymer, a hydrogel, a ceramic or the like), from which the silver is permitted to slowly erode if the sliver comes into contact with a fluid due to a breach in the mechanically tight seal established in the percutaneous bone conduction implant 100.

In one embodiment the silver is ion-sputtered, vacuum deposited and/or powder coated onto the abutment screw 3, the fixture 1 and/or the abutment 2. In yet another embodiment, the abutment screw 3 and/or other components of the percutaneous bone conduction implant 100 could be made out of silver or a silver alloy, providing that a sufficiently anti-microbial effect may be obtained.

In some embodiments, an adsorption process may be utilized to apply some anti-microbial coatings to the components of the percutaneous bone conduction implant 100 (e.g., the parts that are to be coated are put in a liquid containing the antimicrobial agent).

An embodiment provides a long term sustained anti-microbial effect relative to other coatings/coatings applied in other fashions/coatings that are permitted to be exposed to different environments. That is, in embodiments where the anti-microbial coating is substantially isolated from an external environment of percutaneous bone conduction implant 100 (as described in embodiments herein) such that the anti-microbial coating does not elute anti-microbial substances when there is a tight seal between the interior of the percutaneous bone conduction implant and the exterior of the percutaneous bone conduction implant, the anti-microbial coating remains substantially intact. The coating thus exhibits about the same potency/efficacy as possessed by the coating when the percutaneous bone conduction implant was first implanted in the skull of the recipient. This is because the tight seal of the implants described herein prevents initial/ continued moisture intrusion into the interior of the percutaneous bone conduction implant 100. Thus, when a functionally tight seal is present, the coating does not elute anti-microbial material/elutes minimal amounts of anti-microbial material. However, in time (months, and/or years), if the abutment screw 3 becomes loose, or a gap opens permitting the interior of the coupling to be exposed to the exterior environment for any other reason, thereby creating a micro-leakage path, at that time, the anti-microbial coating is about as "new" (e.g., has about the same potency/efficacy) as it was when the percutaneous bone conduction implant 100 was first implanted, and is activated with about the full potency (again, even months and years after initial implantation). This starkly contrasts with application of the anti-microbial coating to components that are frequently exposed/initially exposed/ quickly exposed to moisture, in which case the anti-microbial coating begins to elute and the potency of the anti-microbial coating is relatively quickly reduced.

In the same vein, embodiments include percutaneous bone conduction implants 100 where only trace amounts (nanograms) of silver or other anti-microbial agent can leak out to the soft tissue, thus providing utility to people who are allergic to silver. This also reduces the likelihood that the silver will discolor the skin. By way of comparison, the silver utilized in some embodiments is less than 300 times the silver used in would dressings. In wound dressings, most of the silver is released into the body within a week (as compared to an approximately 6 month period for the silver to leak into soft tissue from the percutaneous bone conduction implant 100, and this only after the interior is exposed to moisture due to a gap opening up).

In some embodiments, anti-microbial coatings utilizing silver do not have a negative effect on the mechanics of the tight seal formed by the components of the percutaneous bone conduction implant 100. For example, the coatings did not significantly (or even noticeably and/or at all) increase the friction between the mating components of the percutaneous bone conduction implant 100. Further, the coating was not damaged when a torque of 30 Ncm was applied to the abutment screw 3 (about a typical torque applied to the abutment screw 3 when the abutment 2 is secured to the fixture 1).

In some embodiments, the silver-based anti-microbial coating kills Staph and Epidermidis and Methicillin resistant Staph Aureus (MRSA).

In some embodiments, the coating is protected from environments containing proteins, even after a micro-leakage path is opened exposing the exterior environment to the interior of the percutaneous bone conduction implant 100. Proteins may tend to neutralize silver ions in a silver-based anti-microbial coating. If the coated surfaces are shielded from proteins/the amount of proteins that are exposed to the coated surfaces is controlled to be low (such as that compared to exposure to proteins in the mouth of the recipient) such as by way of example only and not by way of limitation, location of the percutaneous bone conduction implant 100, the lower the needed concentration of silver is in the coating/the longer the coating will remain potent. That is, if the coatings are exposed to proteins, a higher concentration of silver is needed to obtain the same anti-microbial effect, and thus a lower concentration may be utilized (relative to a coating that will be exposed to proteins at levels that may be found, for example, in the mouth of the recipient).

In some embodiments, the coating is protected from environments containing acids, even after a micro-leakage path is opened exposing the exterior environment to the interior of the percutaneous bone conduction implant 100. Acids may tend to speed the elution of silver from the anti-microbial coating. If the coated surfaces are shielded from acids/the amount of acids that are exposed to the coated surfaces is controlled to be low (such as that compared to exposure to acids in the mouth of the recipient), such as by way of example only and not by way of limitation, location of the percutaneous bone conduction implant 100, the lower the needed concentration of silver is in the coating/the longer the coating will remain potent. That is, if the coatings are exposed to acids, a higher concentration of silver is needed to obtain the same anti-microbial effect, and thus a lower concentration may be utilized (relative to a coating that will be exposed to acids at levels that may be found, for example, in the mouth of the recipient).

By protecting the coating from acids and proteins, a coating that might otherwise last weeks or months may instead last for years.

Various kinds of silver containing compounds can be used in various embodiments. By way of example only and not by way of limitation, silver compounds usable in embodiments include silveroxides, silverperoxides, chlorhexidine-silver sulfadiazines, silverbromides, silverchlorides and other silverhalides or salts of silver.

In yet another embodiment, a zinc or a zinc containing compound is used. Zinc is believed to have a similar anti-microbial effect as silver, or at least an adequate anti-microbial effect, and is also used in wound dressing applications.

In yet another embodiment, interior surfaces of the percutaneous bone conduction implant 100 are anti-adhesive and/or or bacterial repellant. Such may be achieved through the use of poly-ethylene glycol coated surfaces and fluoropolymer coated surfaces (Teflon®, etc.) In some embodiments, the surface is functionalized with a multitude of negatively charged molecules which repel negatively charged bacteria. Electro-polished surfaces are also, to some degree, anti-adhesive, and, in some embodiments, may be used.

In yet another embodiment, an anti-biotic agent such as rifampin, tetracycline, cyclosporine, gentamicin, vancomycin, penicillin or sulfonamide compounds, may be utilized. These compounds may, in such case, be bound to a drug eluting matrix. However, the shelf life of a percutaneous bone conduction implant 100 using such compounds may be short, although, in some applications, sufficiently long to have utility. Anti-biotics are usually sorted into groups based on their chemical or biochemical origin. Antibiotic groups that may be used in an anti-bacterial coating include aminoglycosides, carbapenems, cephalosporines (1st-5th generation), glycopeptides, macrolides, penicillins, quinolones, sulfonamides, tetracyclines, etc.

In one embodiment, anti-microbial/anti-bacterial agents (which may be any of the above-mentioned agents) are contained in a reservoir, such as, for example, in the form of small pores or cavities on the interior surfaces of the percutaneous bone conduction implant 100.

Depending on the type of anti-microbial coating applied to the interior surfaces of the percutaneous bone conduction implant 100, the friction coefficient of those surfaces might be affected. If the coating increases the friction coefficient, the diameter of the abutment screw 3 might be reduced (for instance by way of a "waist" or area of reduced diameter in the mid-section of the abutment screw 3) to achieve "stretching" of the screw. Such stretching is useful for maintaining a safe, long-life stable screw connection. On the other hand, if the coating reduces the friction coefficient, the abutment screw 3 might be designed with an increased diameter which strengthens the abutment screw 3.

It should be understood that in some embodiments, the methods described above for preventing micro-leakage are based on the formation of a mechanically tight seal and/or a surface modification for reducing shear forces and increasing surface area vis-à-vis the implant. If there is an unwanted gap in the system due to failure of the tight seal, loosening of a component or the like (where the gap is formed after implantation), failure to properly implant the percutaneous bone conduction implant (in which case a gap may be present at implantation) the above methods disclosed herein are less effective against micro-leakage.

Further features and capabilities of a bone conduction implant (also referred to as a bone conduction hearing aid) may be found in U.S. Provisional Application No. 60/951,169, entitled "Percutaneous bone conduction implant For a Bone Anchored Hearing Device," filed Jul. 20, 2007, U.S. Provisional Application No. 60/951,163, entitled "Bone Anchor Fixture for a Medical Prosthesis," filed Jul. 20, 2007, and U.S. Patent Application Publication No. 2009-0082817, entitled "Percutaneous bone conduction implant for a Bone Anchored Hearing Device," published on Mar. 26, 2009, which are hereby incorporated by reference herein for application of their teachings, conceptually and/or exactly, to the reduction/elimination of micro-leakage paths, and for the configurations of a percutaneous bone conduction implant disclosed therein. In this regard, embodiments include application of an anti-microbial/bacterial coating or other surface treatment as detailed herein to any interior surface of the components taught in those applications/publications.

In another embodiment, the percutaneous bone conduction implant and/or the bone conduction implant has some or all of the functionality and/or some or all of the structure disclosed in U.S. Pat. No. 4,498,461, the contents pertaining to functionality and structure being incorporated herein by reference.

In another embodiment, the anti-microbial coatings may be utilized in conjunction with any of the other methods/devices/systems disclosed in the above "related art" section.

As noted above, this patent application claims foreign priority to German Patent Application No. 102009014771.3, entitled "Hearing Aid Implant," filed on 25 Mar. 2009, the entire contents of that German Patent Application being incorporated by reference herein.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. All patents and publications discussed herein are incorporated in their entirety by reference thereto.

What is claimed is:

1. A percutaneous bone conduction implant, comprising:
   a fixture configured to be anchored in the recipient's skull; and
   a skin-penetrating abutment configured to interface with the fixture and to permit the abutment to be removably attached to the fixture to form a fixture-abutment assembly,
   wherein at least one anti-microbial surface forms one or more surfaces of the formed fixture-abutment assembly located in an interior of the formed fixture-abutment assembly when the fixture is removably attached to the abutment with an abutment screw, the interior being substantially isolated from a surrounding environment of the fixture-abutment assembly, and
   wherein one of the fixture and the skin-penetrating abutment is seated within a cavity of the other of the fixture and the skin-penetrating abutment such that abutting surfaces of the fixture and the skin-penetrating abutment interface together to form a mechanically tight fit.

2. The percutaneous bone conduction implant of claim 1, wherein the fixture-abutment assembly includes an abutment screw, and wherein the at least one anti-microbial surface is located on the abutment screw.

3. The percutaneous bone conduction implant of claim 1, wherein the abutment has a substantially conical surface, located on the exterior of the abutment relative to the abutment, with a tapered exterior contour dimensioned to fit within a tapered interior contoured surface of a cavity of the fixture to provide a mechanically tight fit when the abutment is removably attached to the fixture, wherein the at least one anti-microbial surface is located at the interface of the conical exterior of the abutment and the tapered interior contoured face of the fixture.

4. The percutaneous bone conduction implant of claim 1, wherein a first part of the fixture located opposite screw threads of the fixture and a first part of the abutment located adjacent to the first part of the fixture interface with each other with a conical fit when the abutment is removably attached to the fixture to form the fixture-abutment assembly, wherein the at least one anti-microbial surface is located at the interface of the first parts.

5. The percutaneous bone conduction implant of claim 1, wherein the interior of the formed fixture-abutment assembly is a closed environment hermetically isolated from an external environment of the formed fixture-abutment assembly.

6. The percutaneous bone conduction implant of claim 1, wherein the at least one anti-microbial surface is substantially isolated from an external environment of the formed fixture-abutment assembly such that the anti-microbial coating does not elute anti-microbial substances when there is a tight seal between the interior of the formed fixture-abutment assembly and the exterior of the formed fixture-abutment assembly.

7. The percutaneous bone conduction implant of claim 1, wherein the at least one anti-microbial surface is anti-microbially activated only when exposed to moisture, and wherein the interior of the formed fixture-abutment assembly is substantially isolated from an external environment of the formed fixture-abutment assembly such that the at least one anti-microbial surface in the interior is not exposed to moisture and therefore is not anti-microbially activated.

8. The percutaneous bone conduction implant of claim 1, wherein the at least one anti-microbial surface comprises silver.

9. The percutaneous bone conduction implant of to claim 1, wherein the at least one anti-microbial surface is contained in a reservoir in the fixture-abutment assembly.

10. The percutaneous bone conduction implant of to claim 2, wherein the abutment screw is made substantially of an anti-microbial material.

11. The percutaneous bone conduction implant of claim 10, wherein the abutment screw is made substantially of silver or a silver alloy.

12. The percutaneous bone conduction implant of claim 1, wherein the at least one anti-microbial surface comprises an anti-microbial coating, and wherein the anti-microbial coating has a first thickness corresponding to a first estimated efficacy achieved during exposure to an environment substantially devoid of proteins and acids, and wherein the first thickness is substantially less than a second thickness of an anti-microbial coating corresponding to a second estimated efficacy achieved during exposure to least one of proteins and acids, wherein the first estimated efficacy is about the same as the second estimated efficacy.

13. The percutaneous bone implant of claim 1, wherein the anti-microbial surface is limited to interior surfaces of the formed fixture.

14. A percutaneous bone conduction implant, comprising:
a fixture configured to be anchored in the recipient's skull; and
a skin-penetrating abutment configured to interface with the fixture and to permit the abutment to be removably attached to the fixture to form a fixture-abutment assembly,
wherein the abutment includes a first coupling portion adapted to receive a second coupling portion of a bone conduction device and to establish a mechanical connection with the bone conduction device,
and wherein at least one anti-microbial surface is present in the formed fixture-abutment assembly and located in an interior of the formed fixture-abutment assembly when the fixture is removably attached to the abutment with an abutment screw, the interior being substantially isolated from a surrounding environment of the fixture-abutment assembly, and
wherein one of the fixture and the skin-penetrating abutment is seated within a cavity of the other of the fixture and the skin-penetrating abutment such that abutting surfaces of the fixture and the skin-penetrating abutment interface together to form a mechanically tight fit.

15. The percutaneous bone conduction implant of claim 14, wherein the at least one anti-microbial surface is configured to kill at least 99% of all bacteria by quantity that come into contact with the at least one anti-microbial surface.

16. The percutaneous bone conduction implant of claim 14, wherein the at least one anti-microbial surface is located on surfaces that are at least one of on or adjacent to an abutment screw configured to screw into the fixture to releasably attach the abutment to the fixture, wherein the friction coefficient of the least one anti-microbial surface is about the same as the friction coefficient which would be present at the same surfaces without the at least one anti-microbial surface.

17. The percutaneous bone conduction implant of claim 14, the friction coefficient of the surfaces with the at least one anti-microbial surface is the same as the friction coefficient which would be present at the same surfaces without the at least one anti-microbial surface.

18. The percutaneous bone conduction implant of claim 14, wherein the at least one anti-microbial surface is a silver-based anti-microbial surface that kills Staph and Epidermidis and Methicillin resistant Staph Aureus (MRSA).

19. The percutaneous bone implant of claim 14, wherein the anti-microbial surface is limited to interior surfaces of the formed fixture.

20. A percutaneous bone conduction implant, comprising:
a fixture configured to be anchored in the skull of the recipient; and
a skin-penetrating abutment configured to interface with the fixture and to permit the abutment to be removably attached to the fixture to form a fixture-abutment assembly through which controlled vibrations can be directly transmitted from outside the recipient's body directly into the fixture-abutment assembly,
wherein the abutment is dimensioned to extend from the fixture to above an outer skin layer of the recipient when the fixture-abutment is located at a first body location located approximately adjacent a recipient's pinna and the fixture is anchored in the recipient's skull, and
wherein one of the fixture and the skin-penetrating abutment is seated within a cavity of the other of the fixture and the skin-penetrating abutment such that abutting surfaces of the fixture and the skin-penetrating abutment interface together to form a mechanically tight fit.

21. The percutaneous bone implant of claim 20, further comprising at least one anti-microbial coating along one or more interior surfaces of the fixture.

22. The percutaneous bone conduction implant of claim 20, further including an abutment screw adapted to extend through the abutment and screw into the fixture to removably attach the abutment to the fixture, wherein when the abutment screw is screwed into the fixture so that the abutment sealingly interfaces with the fixture to form the fixture-abutment assembly, a micro-leakage pathway is present, wherein the fixture-abutment is located at the first body location, extending from outside the recipient to a region between facing surfaces of the abutment screw and the abutment to at least one of (i) a region between facing surfaces of the abutment screw and the fixture and (ii) a region between facing surfaces of the abutment and the fixture,
wherein the at least one anti-microbial surface is located within the micro-leakage pathway.

23. An implanted percutaneous bone conduction implant, comprising:
- a fixture-abutment assembly implanted in the recipient's skull at a first body location, wherein the fixture-abutment assembly includes:
  - a fixture anchored in the recipient's skull; and
  - a skin-penetrating abutment releasably attached to the fixture extending from beneath a surface layer of an epidermis of the recipient to an exterior of the recipient above the surface layer of the epidermis of the recipient at the first body location,
- wherein one or more anti-microbial surfaces are present on the fixture-abutment, the one or more surfaces being located in an interior of the formed fixture-abutment assembly when the fixture is removably attached to the abutment, the interior being substantially isolated from a surrounding environment of the fixture-abutment assembly, and
- wherein one of the fixture and the skin-penetrating abutment is seated within a cavity of the other of the fixture and the skin-penetrating abutment such that abutting surfaces of the fixture and the skin-penetrating abutment interface together to form a mechanically tight fit.

24. The percutaneous bone implant of claim 23, wherein the anti-microbial surface is limited to interior surfaces of the formed fixture.

25. The percutaneous bone conduction implant of claim 23, wherein the first location is located approximately behind a pinna of the human body.

26. The percutaneous bone conduction implant of claim 23, wherein the least one anti-microbial surface is anti-microbially activated only when exposed to moisture, and wherein the interior of the formed fixture-abutment assembly is substantially isolated from an external environment of the formed fixture-abutment assembly such that the at least one anti-microbial surface in the interior is not exposed to moisture and therefore is no anti-microbially activated.

27. A method of implanting a percutaneous bone conduction implant, comprising:
- anchoring a fixture in a recipient's skull; and
- releasably attaching a skin-penetrating abutment to the fixture to form a fixture-abutment assembly,
- wherein the action of releasably attaching the skin-penetrating abutment to the fixture includes establishing a hermetically sealed interior in the formed fixture-abutment assembly,
- wherein at least one anti-microbial surface is present on an interior of the formed fixture-abutment assembly, the interior initially being hermetically sealed from an exterior of the formed fixture-abutment assembly, and
- wherein, after a period of time after releasably attaching the skin-penetrating abutment to the fixture, the interior ceases to be hermetically sealed from the exterior of the formed fixture-abutment assembly while the skin-penetrating abutment is still releasably attached to the fixture, and
- wherein one of the fixture and the skin-penetrating abutment is seated within a cavity of the other of the fixture and the skin-penetrating abutment such that abutting surfaces of the fixture and the skin-penetrating abutment interface together to form a mechanically tight fit.

28. The method of claim 27, wherein the period of time is over about one year.

29. The method of claim 28, wherein after the period of time, the at least one anti-microbial surface has about the same efficacy with respect to killing microbes as possessed by the surface when the abutment was releasably attached to the fixture.

30. The method of claim 27, wherein the anti-microbial surface is silver-based, the method further comprising avoiding exposure of the at least one anti-microbial surface to at least one of proteins and acids.

31. A percutaneous bone conduction implant, comprising:
- a fixture configured to be anchored in a recipient's skull; and
- a skin-penetrating abutment configured to interface with the fixture and to permit the abutment to be removably attached to the fixture to form an fixture-abutment assembly through which controlled vibrations can be directly transmitted from outside the recipient's body directly into the fixture-abutment assembly,
- wherein the formed fixture-abutment assembly includes one or more surfaces located in an interior of the formed fixture-abutment assembly when the fixture is removably attached to the abutment with an abutment screw, the interior being substantially isolated from a surrounding environment of the fixture-abutment assembly, and
- wherein at least one of the one or more surfaces are at least one of anti-adhesive, bacterial repellant or coated with an antibiotic agent, and
- wherein one of the fixture and the skin-penetrating abutment is seated within a cavity of the other of the fixture and the skin-penetrating abutment such that abutting surfaces of the fixture and the skin-penetrating abutment interface together to form a mechanically tight fit.

32. The method of claim 27, wherein the anti-microbial surface is limited to interior surfaces of the formed fixture.

33. The percutaneous bone implant of claim 31, wherein the one or more surfaces is one or more anti-microbial surfaces limited to interior surfaces of the formed fixture.

* * * * *